United States Patent [19]

Boslau

[11] 4,155,365
[45] May 22, 1979

[54] ARTIFICIAL RESPIRATION APPARATUS

[76] Inventor: Rodney J. Boslau, 2601 W. Boise Ave., Space E, Boise, Id. 83706

[21] Appl. No.: 790,708

[22] Filed: Apr. 25, 1977

[51] Int. Cl.² ............................................. A61M 16/00
[52] U.S. Cl. .................................................... 128/351
[58] Field of Search ........ 128/349 B, 349 BV, 348 R, 128/145.5, 145.7, 145.8, 351

[56] References Cited

U.S. PATENT DOCUMENTS

| | | | |
|---|---|---|---|
| 2,936,760 | 5/1960 | Gants | 128/349 B |
| 3,683,908 | 8/1972 | Don Michael et al. | 128/145.7 |
| 3,905,361 | 9/1975 | Hewson et al. | 128/351 X |
| 4,090,518 | 5/1978 | Elam | 128/349 B |

FOREIGN PATENT DOCUMENTS 1505607  12/1967  France ....................................... 128/351

*Primary Examiner*—Henry J. Recla
*Attorney, Agent, or Firm*—Paul F. Horton

[57] ABSTRACT

Apparatus for use in artificial respiration comprising an elongated tubular member for insertion into the esophagus having a pair of expandable elements for sealing the esophagus and pharynx against air loss. The tubular member includes an air passage between an external air source and discharge openings located between the expandable elements for introducing air to the lungs. The apparatus may also contain a gastric intubation tube, and external means for inflating the expandable elements with or without syringes.

4 Claims, 3 Drawing Figures

ARTIFICIAL RESPIRATION APPARATUS

BACKGROUND OF THE INVENTION

1. Field of the Invention

This invention relates, in general, to emergency forced respiration devices, and in particular, to esophageal, intubation respirators.

2. Description of the Prior Art

The value of artifical respiration in emergency situation has long been recognized. Recent advances include the invention of Don Michael et al, U.S. Pat. No. 3,683,908 which provides an esophageal tube having an inflatable cuff for sealing the esophagus and air discharge ports for providing air to the lungs. Also among the recent advances is the modification of the Michael tube by Hewson, U.S. Pat. No. 3,905,361, which provides ventilation to the lungs through a face mask without a special duct. The Don Michael invention discloses no means for preventing the air forced through the air discharge passages from exiting through nose or mouth except mouth shield 14. The Hewson invention attempts to prevent air escape by means of a mask covering nose and mouth. Problems inherent in the current art include air leakage through the nose and mouth because of an inadequate exterior seal on the face. Variations in facial size and configuration complicate the problem.

SUMMARY OF THE INVENTION

The present invention comprises a tube for esophageal insertion which has an inner cuff for sealing the lower esopagus, an outer cuff for sealing the upper respiratory tract, and means for ventilating the lungs through air discharge ports located between the two cuffs. A gastric evacuation tube and automatic cuff inflators are also provided.

It is therefore an object of the present invention to provide an esophageal airway having a pair of inflatable cuffs for preventing air excape either into the stomach or into the atmosphere.

It is a more particular object to provide an esophageal airway having an upper respiratory seal.

A further object of the present invention is to provide an upper respiratory seal that requires no external manipulation.

Another object of the present invention is to provide artifical respiration apparatus having esphageal and upper respiratory seals, an air passage, and a gastric evacuation tube.

Other objects will become apparent and a more thorough and comprehensive understanding may be had from the following description taken in conjunction with the accompanying drawings forming a part of this specification.

DETAILED DESCRIPTION OF THE INVENTION

Figure 1:
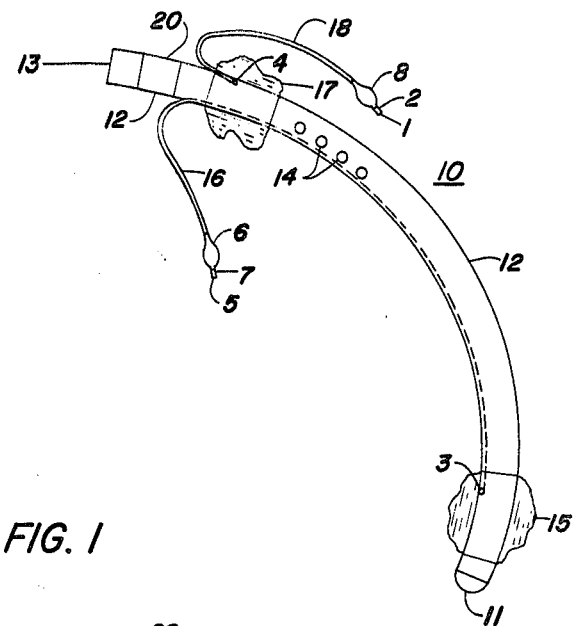
FIG. 1 is a perspective view, partly in section, of one embodiment of the present invention.

Refering now to FIG. 1, one preferred embodiment of the respiration apparatus 10, made according to the present invention is disclosed. Respiration apparatus 10 includes elongated tube member 12 for insertion into the esophagus, first expandable element 15, second expandable element 17, inflating tubes 16 and 18, air inlet 13 and air outlet ports 14.

Elongated tube member 12 is formed of synthetic plastic having a degree of flexibility to permit insertion into the esophagus. Tube 12 has, at its inner, a rounded tip portion 11 which facilitates insertion as well as sealing tube 12 to prevent air inflow into the stomach. Tube 12 contains at its outer end, adapter 20, a more rigid plastic tube than tube member 12, which, in operation, is connected to an air bag for lung ventilation. Rigid adapter 20, in addition, serves as a bite-tube thereby preventing accidental collapse or closing of tube member 12. Adapter 20 may also contain apparatus for inflating expandable elements 15 and 17 as will hereinafter be explained.

Adjacent the inner end of tube member 12, and around its outside, there is provided first expandable element 15 which may be an inflatable balloon formed of rubber, synthetic plastic, or like material. A small hole 3 in tube member 12 connects balloon 15 to small bore tube 16 connected to the interior wall of tube member 12. Small bore tube 16 emerges from tube 12 adjacent its outer end where tube 16 connects with inflatable pressure indicator 6. Indicator 6 contains syringe adapter 7 which may be either attached to a syringe, not shown, for inflation, or air tight blocking element 5 preventing air flow from balloon 15. Blocking element 5 may consist of a removable check valve.

Adjacent the outer end of tube member 12 and around its outside there is provided second expandable element 17, which, like element 15, may be an inflatable balloon. A small hole 4 connects balloon 17 to small bore tube 18 connected to the interior wall of tube 12. Small bore tube 18 emerges from tube 12 adjacent its outer end where tube 18 connects with inflatable pressure indicator 8. Indicator 8 contains syringe adapter 2 which may be attached to a syringe or blocking element 1.

Tube 12, between balloons 15 and 17, is provided with a plurality of apertures 14 along its length and around its peripheral walls. Apertures 14 extend into the interior of tube 12 and thereby provide fluid communication with outlet 13 for lung ventilation.

Figure 2:
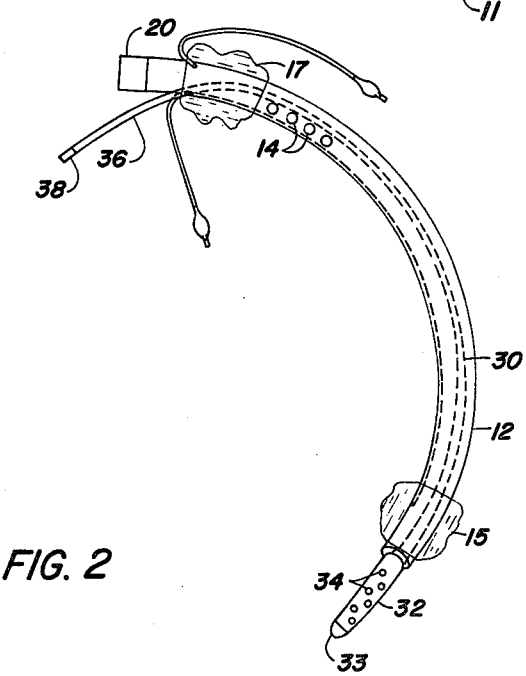
FIG. 2 is a perspective view of the device in FIG. 1, including a gastric evacuation tube.

Referring now to FIG. 2, a modification of device 10 is disclosed. The modification includes gastric tube 30. Tube 30 extends substantially co-axially with tube 12 and has an inner end 32 extending through the distal tip of tube 12, thereby replacing rounded tip portion 11 of FIG. 1. Inner end 32 contains a blunted end 33 for closing the tip of gastric tube 30 and facilitating tube insertion. Inner end 32 contains a plurality of apertures 34 along its length and extending through its peripheral walls providing fluid communication to the interior of tube 30. At its opposite and outer end 36 which exits adjacent adapter 20, tube 30 may contain a syringe adapter 38 for syringe attachment. When inserted in place, apertures 34 are disposed inside the stomach and provide ports through which stomach contents, including any air which might leak from the esophagus around air balloon 15, may be asperated.

Figure 3:
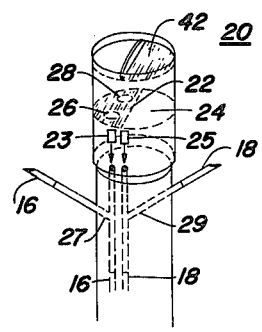
FIG. 3 is a sectional perspective view of the exterior adapter of the present invention.

Adapter 20, shown to advantage in FIG. 3 may include apparatus to fill balloons 15 and 17 by means of air forced through inlet 13 rather than by means of a syringe connected to adapters 2 and 7, best seen in FIG. 1. This inflating apparatus includes a disc 22 having a main air supply port 24 communicating between air inlet 13 and the interior of tube 12 and thus to apertures 14 and the lungs, and two ports 26 and 28 communicating between air inlet 13 and tubes 16 and 18 extending to balloons 15 and 17 respectively. Disc 22 is secured to the interior of the side walls of adapter 20, transversely to the duct. Means for connecting ports 26 and 28 to said tubes 16 and 18, respectively, include Y-connectors 27 and 29 provided as inserts into tubes 16 and 18. One-way check valves 23 and 25 prevent air leakage from balloons 15 and 17. Also included is port cover 42 which is rotatably secured by means of slot or otherwise to proximally engage disc 22. Cover 42 is formed so as to selectively cover one or more of ports 24, 26 or 28 at any one time, the purpose being to block air passage to the lungs while forcing air into balloon inflating ports 26 and 28 and vica versa.

In operation, tube member 12 is inserted into the esophagus so that tip 32 of gastric tube 30 is located within the stomach. Balloons 15 and 17 are then inflated in one of two ways. The balloons may be inflated by connecting a syringe to each of the adapters 2 and 7 and forcefully inserting air. Indicators 6 and 8 allow proper gauging of the amount of air to be inserted. Alternately, where adapter 20 contains means for inflating the balloons through inlet 13, as shown in FIG. 3, cover 42 is rotated to cover port 24 going to the lungs and thereby uncover ports 26 and 28 going to the balloons. Air is forced through inlet 13 by means of bellows, air bag, or otherwise through check valves 23 and 25, through the Y-connectors and into the balloons. Check valves 5 prevent air escape through indicators 6 and 8. When the balloons are sufficently inflated as determined by the indicators, port cover 42 is rotated to cover port holes 26 and 28 and to open port hole 24 going to the lungs. In this manner, balloons 15 and 17 are not further inflated. It will be seen then balloon 15 seals the esophagus from the stomach and balloon 17 seals the pharyngeal cavity from the atmosphere so that artificial respiration can then be performed by inflating and deflating the lungs through outlet 13 by breathing into the outlet, or attaching a respirator such as an air bag or bellows. Gastric fluid may be extracted, at will, by means of a syringe attachable to adapter 38, shown in FIG. 2. Device 10 is removed by removing blocking element 5 permitting the balloons to deflate and then withdrawing the tube.

Having thus described in detail a preferred embodiment of the present invention, it is to be appreciated and will be apparent to those skilled in the art that many physical changes could be made in the apparatus without altering the inventive concept and principle embodied therein. The present embodiment is therefore to be considered in all respects as illustrative and not restrictive, the scope of the invention being indicated by the appended claims rather than by the foregoing description, and all changes which come within the meaning and range of equivalency of the claims are therefore to be embraced therein.

I claim:

1. Apparatus for medical purposes comprising:
   an elongated tubular member for insertion into the esophagus, said tubular member having a closed inner end and an open outer end;
   a first expandable element carried by the tubular member adjacent its inner end and operable to form an effective seal with the walls of the esophagus;
   a second expandable element carried by the tubular member adjacent its outer end and operable to form an effective seal with the walls of the pharynx;
   at least one air outlet port in the side wall of the tubular member located between said first and second expandable elements providing fluid communication to a subject's lungs;
   a first and second conduit carried by and extending along the tubular member, each conduit having an outer end adapted to connect to an external inflator unit and an inner end in fluid communication with said first expandable element and said second expandable element, respectively; and
   a resuscitator inflator adapter connected to said outer end of said elongated tubular member, said adapter including an air inlet port attachable to an inflator, an air outlet port providing fluid communication between the inflator and the open end of said tubular member for forcing air to and withdrawing air from the subject's lungs and a pair of expandable element ports, each of said expandable element ports including a duct communicating said air inlet port with one of said conduits for inflating said first and second expandable elements with air, and each of said ports including one-way valve means for retaining the air in said expandable elements.

2. The apparatus of claim 1 further comprising port closure means for selectively closing said air outlet port and said expandable element ports.

3. The apparatus of claim 1 further comprising a gastric tube carried by said elongated tubular member, said gastric tube having a proximal opening and a distal opening in fluid communication with one another, said distal opening located blow said first expandable element and said proximal opening located above said second expandable element.

4. The apparatus of claim 1 further comprising a pair of expandable chambers, each chamber connected to one of said conduits adjacent the outer end of said conduit to prevent overpressurizing said first and second expandable elements.

* * * * *